US012685552B2

(12) United States Patent
Schneider et al.

(10) Patent No.: US 12,685,552 B2
(45) Date of Patent: Jul. 21, 2026

(54) INPUT UNIT FOR A MEDICAL INSTRUMENT, AND MEDICAL SYSTEM COMPRISING AN INPUT UNIT

(71) Applicant: KARL STORZ SE & CO. KG, Tuttlingen (DE)

(72) Inventors: Janosz Schneider, Donaueschingen (DE); Dominik Längle, Mülheim (DE); Sven Axel Grüner, Trossingen (DE); Jochen Stefan, Wald (DE); Thorsten Ahrens, Wurmlingen (DE)

(73) Assignee: KARL STORZ S.E. & Co. KG, Tuttlingen (DE)

( * ) Notice: Subject to any disclaimer, the term of this patent is extended or adjusted under 35 U.S.C. 154(b) by 215 days.

(21) Appl. No.: 18/291,695

(22) PCT Filed: Jul. 25, 2022

(86) PCT No.: PCT/EP2022/070827
§ 371 (c)(1),
(2) Date: Jan. 24, 2024

(87) PCT Pub. No.: WO2023/006681
PCT Pub. Date: Feb. 2, 2023

(65) Prior Publication Data
US 2025/0082353 A1 Mar. 13, 2025

(30) Foreign Application Priority Data
Jul. 28, 2021 (DE) ......................... 102021119618.3

(51) Int. Cl.
*A61B 17/30* (2006.01)
*A61B 17/00* (2006.01)

(52) U.S. Cl.
CPC .... *A61B 17/30* (2013.01); *A61B 2017/00367* (2013.01); *A61B 2017/00424* (2013.01); *A61B 2017/305* (2013.01)

(58) Field of Classification Search
CPC .......... A61B 17/30; A61B 2017/00367; A61B 2017/00424; A61B 2017/305;
(Continued)

(56) References Cited

U.S. PATENT DOCUMENTS

| | | | |
|---|---|---|---|
| 5,454,827 A | 10/1995 | Aust et al. | |
| 2003/0195664 A1* | 10/2003 | Nowlin .................. | A61B 34/37 318/568.11 |

(Continued)

FOREIGN PATENT DOCUMENTS

| | | |
|---|---|---|
| DE | 10 2019 121 092 A1 | 2/2021 |
| EP | 2823772 A1 | 1/2015 |

(Continued)

OTHER PUBLICATIONS

International Search Report, Application No. PCT/EP2022/070827, mailed Nov. 17, 2022. ISA/European Patent Office, 5 pages.
(Continued)

*Primary Examiner* — Andrew Restaino
(74) *Attorney, Agent, or Firm* — Brooks Kushman P.C

(57) ABSTRACT

An input unit for operating a medical instrument includes: a hollow shaft extending along a longitudinal axis for receiving steering wires; a tool arranged at the distal end of the shaft and formed along an axis of extent; and a control unit, which is arranged at the proximal end of the shaft, for manipulating the tool by means of the steering wires. The input unit comprises first input means for continuously converting, in a pivotally and/or rotationally true manner and preferably without interruption and/or absolutely, an ergonomically limited user input, in particular a natural user (Continued)

movement of movable first operating means, into an adjust-
ment movement of the tool in a first handling mode, in order
to pivot the tool to a limited extent relative to the longitu-
dinal axis and/or rotate it to a limited extent about the axis
of extent by means of the control unit.

10 Claims, 5 Drawing Sheets

(58) Field of Classification Search
CPC .............. A61B 34/71; A61B 2090/033; A61B
2090/035; A61B 34/70
See application file for complete search history.

(56) References Cited

U.S. PATENT DOCUMENTS

| | | | | |
|---|---|---|---|---|
| 2019/0069968 A1* | 3/2019 | Sholev | .................... | A61B 34/71 |
| 2019/0350662 A1* | 11/2019 | Huang | .................... | A61B 34/74 |
| 2020/0237461 A1* | 7/2020 | Kadokura | .............. | A61B 34/37 |
| 2020/0360038 A1* | 11/2020 | Yuan | .................. | A61B 17/2909 |

FOREIGN PATENT DOCUMENTS

| | | | |
|---|---|---|---|
| EP | 3488808 A1 | 5/2019 |
| WO | 2020218920 A2 | 10/2020 |

OTHER PUBLICATIONS

International Preliminary Report on Patentability, Application No.
PCT/EP2022/070827, mailed Jan. 18, 2024. ISA/European Patent
Office.

* cited by examiner

Fig. 1

INPUT UNIT FOR A MEDICAL INSTRUMENT, AND MEDICAL SYSTEM COMPRISING AN INPUT UNIT

CROSS-REFERENCE TO RELATED APPLICATIONS

This application is the U.S. national stage of PCT/EP2022/070827 filed on Jul. 25, 2022, which claims priority of German Patent Application No. 10 2021 119 618.3 filed on Jul. 28, 2021, the contents of which are incorporated herein.

TECHNICAL FIELD

The present disclosure relates to an input unit for operating a medical instrument according to the preamble of claim 1. The present disclosure further relates to a medical system comprising at least one input unit according to the disclosure and at least one medical instrument.

BACKGROUND

An input unit of the type in question for operating a medical instrument is known, for example, from U.S. Pat. No. 5,454,827 A.

The known medical instrument comprises a hollow shaft extending along a longitudinal axis for receiving steering wires, wherein the distal end of the shaft has a tool formed along an axis of extent, and the proximal end of the shaft has a control unit, which is designed for manipulating the tool by means of the steering wires. The control unit has a spatially adjustable plate, which is coupled to four steering wires and can pivot the tool relative to the longitudinal axis via pivot members arranged at the distal end.

For controlling the manipulation of the medical instrument, an input unit of the type in question is provided with first input means, which an operator can operate by hand. Thus, ergonomic user inputs from the operator are converted continuously, i.e. in a pivotably and/or rotationally true manner, into the manipulation of the tool. In addition to just pivoting the tool in order to influence the orientation, the tool can also be manipulated via operating means that interact with the index finger of the operator, for example in order to adjust a tool, designed as a jaw part, between an open and a closed state. Moreover, a limited rotation of the tool can be implemented by the rotation of the gripped input unit, wherein the rotation is represented by the natural freedom of movement of the hand and/or arm of the operator.

In the control of the medical instrument, the adjustment movements of the tool thus always follow the natural movements of the hand and/or arm of the operator, specifically in an uninterrupted and/or absolute manner. In other words, the mechanically coupled tool continuously follows the operator's ergonomically limited user inputs, so that the operator always has control of the tool, thus enabling precise working in the operating field.

The input units of the type in question thus enable the precise execution of minimally invasive medical operations, for example in order to take tissue samples, to suture tissue or to perform other surgical actions in a sensitive environment.

The disadvantage of the known input unit is the limited and/or restricted manipulation of the tool, since it entails a pivotably and rotationally true conversion of the natural movement of the user, which is why, in addition to the mechanical and/or design limitations of the tool, there is a restriction due to the degree of the natural freedom of movement of the operator.

Moreover, medical instruments are also known which in some regions, by means of a spindle, permit a mechanically limited rotation of the tool for a limited rotation range. For control purposes, input units are used that enable rotationally accurate control of the tool, wherein, in order to overcome the operator's restricted freedom of movement, an interruption occurs in the control, since the operator grasps the first input means or there is a short interruption and/or decoupling between the input unit and the tool for a reset and/or return of the first input means, which is always associated with a brief loss of control over the tool.

Moreover, there is in the meantime a promising further development of the described medical instrument, this development being described in DE 10 2019 121 092 A1 of the applicant. Simply put, an improved mechanism now allows the tool to rotate endlessly about its axis of extent. Advantageously, the rotation of the tool can also be carried out independently of the pivoting of the tool, which is why the range of use of the medical instrument is considerably expanded. The control of a medical instrument developed in this way is now problematic, since an endless rotation can no longer be controlled by the pivotably and/or rotationally true conversion of the user movement. Since in most cases two tools are controlled by the operator in the operating field, one in each hand, control by means of two-handed operation is ruled out. Moreover, the operator should always retain control of the tool so that, independently of controlling the endless rotational movement of the tool, there is always an uninterrupted coupling between the first input means and the tool, in order to apply the user movements to the tool in a pivotably and/or rotationally true manner.

SUMMARY

The object of the present disclosure is therefore to propose an input unit which overcomes the disadvantages known from the prior art. In particular, it is the object of the present disclosure to provide an input unit which permits the control of an endless rotation of the tool despite the continuous, pivotably and/or rotationally true conversion of a user input.

Moreover, the object is to provide a medical system comprising at least one input unit according to the disclosure and at least one medical instrument.

This object is achieved by an input unit having the features of claim 1. Moreover, the object is achieved by a medical system according to the disclosure.

Advantageous developments of the disclosure are set forth in the dependent claims. The scope of the disclosure covers all combinations of at least two of the features disclosed in the description, the claims and/or the figures.

In the context of the present disclosure, it is intended to provide an input unit with first input means and second input means. The input unit according to the disclosure is designed for operating a medical instrument which comprises a hollow shaft extending along a longitudinal axis for receiving steering wires, wherein a tool extending along an axis of extent is arranged at a first or distal end of the shaft. Moreover, a control unit for manipulating the tool by means of the steering wires is provided at a second or proximal end of the shaft. The first input means according to the disclosure are designed for continuous, pivotably and/or rotationally accurate conversion of an ergonomically limited user input of an operator into an adjustment movement of the tool in a first handling mode, in order to pivot the tool relative to the longitudinal axis and/or rotate it about the axis of extent through the first input means by means of the steering wires and via the control unit. On account of the structural design of the in parts rigidly formed shaft, a pivoting of the tool with respect to the longitudinal extent of the shaft is possible only over a limited pivoting range. Moreover, the rotation of the tool is also possible only over a limited rotation range, which is limited by the natural mobility of the operator, in particular of a hand of the operator gripping the first operating means, which mobility, in respect of the continuous, i.e. absolute, introduction of rotation, is limited on account of the structure of the human arm in relation to the rotation range.

According to the disclosure, operating means for manipulating the tool are provided as the first input means which continuously, i.e. without interruption in the coupling between the operating means and the tool, translate, convert and/or transform the ergonomically limited user input into the manipulation of the tool.

According to the present disclosure, the first input means are formed by a tweezer element coupled to a gimbal suspension via a support element, wherein the tweezer element has two leg sections, which are suspended pivotably relative to each other via a bearing unit, such that an operator of the input unit according to the disclosure can effect a pivoting movement of the two leg sections by gripping the two tweezer elements between thumb and index finger for the purpose of applying a force to manipulate the tool. In this context, it is preferably provided within the scope of the present disclosure that the tool is designed as a jaw part, wherein the closing position of the jaw part can be controlled by the pivoting of the two leg sections.

Moreover, the tweezer element according to the disclosure comprises a pistol grip section which is arranged and/or oriented relative to the two leg sections such that the palm of the operator is supported when carrying out the ergonomically limited user input in the first handling mode. According to the disclosure, this improves the control of the tool in the first handling mode since, when carrying out the pivoting and/or rotational movements, the force input from the hand of the operator to the first input means is improved by the pistol grip section, which is why the tweezer element, together with the pistol grip section, is movable precisely about the three pivot axes of the gimbal suspensions.

Moreover, the second input means are designed for at least partial, not absolute conversion of at least one further user input into an endless rotational movement of the tool about its axis of extent in a second handling mode.

According to the disclosure, the second input means are advantageously arranged as second operating means either directly on the pistol grip section or in one of the two leg sections.

Advantageously, the pistol grip section makes it possible to improve the handling and/or ergonomics of the tweezer element according to the disclosure, in particular to permit precise control of the tool during long operating periods. Moreover, the pistol grip section, having a positive effect on the first handling mode, can additionally receive the second operating means, which are designed for controlling the tool in the second handling mode.

In a further development of the present disclosure, the second operating means are formed by a rotary element, in particular a rotary wheel, a gauge wheel or a partially rotatable rocker element, which is received by the pistol grip section, in particular by a lateral outer surface of the pistol grip section, such that it protrudes in some regions, in such a way that it can be operated, i.e. rotated or actuated, in the working position of the operator, by the remaining fingers of the hand used to pivot the leg sections, in order to capture the further user input by operation of the rotary element.

By virtue of the rotary element formed, which can be operated independently of the tweezer element and the gimbal suspension, the tool can be operated in the second handling mode independently of the first handling mode, in order thereby to control the endless rotation of the tool.

In this context, it is further provided that the rotary element is mounted rotatably about an axis of rotation, and the axis of rotation axis extends substantially parallel to a longitudinal extension of the pistol grip section. The rotary element can thus be advantageously rotated by means of the free, i.e. unused, fingers of the hand of the operator. The orientation permits particularly ergonomic operation of the second input means for controlling the tool in the second handling mode.

The rotary element is preferably formed as a rotary wheel or as a gauge wheel. The rotary wheel is preferably rotatable endlessly about the axis of rotation, wherein the endless rotation of the tool can be controlled by the direction of rotation and the speed of rotation of the rotary wheel.

In the preferred embodiment of the rotary element as a gauge wheel, the direction of rotation of the tool is defined by two rotation regions of the gauge wheel. Thus, the gauge wheel can be rotated from a central rest position in two opposite directions of rotation to at least one end position or adjustment position, wherein a continuous rotational movement of the tool is activated in the respective end position or adjustment position. Particularly preferably, two or more adjustment positions are provided in which the continuous rotation of the tool can be activated with different speeds of rotation.

In an alternative, preferred embodiment of the present disclosure, the second operating means are formed by at least one switch element, which is designed for switching between the first handling mode and the second handling mode. Advantageously, the rotation mechanism of the gimbal suspension can thus be used not only for detecting rotational movements in the first handling mode but also for controlling the second handling mode. In this case, after the control of the second handling mode is actuated by actuation of the switch element, the tweezer element, together with the pistol grip section, can be rotated to a left adjustment position and to a right adjustment position, wherein, in the left adjustment position, the activation of a left endless rotational movement of the tool is activated, and, in the right adjustment position, the activation of a right endless or continuous rotational movement of the tool is activated. In this case, there is therefore a decoupling between the user movement and the rotational movement of the tool.

By contrast, in the first handling mode there is a rotationally accurate transfer of the user's movement onto the tool, which can therefore only be rotated as far as the freedom of movement of the hand and/or arm of the operator allows.

Alternatively, the second operating means can also be formed by a first switch element and a second switch element. In this context, it is preferred if the first switch element is designed such that, by permanent or brief actuation of the first switch element, a first switching state can be activated in order to activate a permanent left rotational movement of the tool, and if the second switch element is designed such that, by permanent or brief actuation of the second switch element, a second switching state can be activated in order to activate a permanent right rotational movement of the tool. Moreover, the first and the second switch element are designed such that, in a third switching state, the tool does not perform a rotational movement, in order to control a gripping and/or cutting functionality by means of the tweezer interacting with thumb and index finger in the third switching state in the preferred embodiment of the tool as a jaw part. In other words, it is preferably possible to activate a rotational movement of the tool in the left direction by the permanent or brief actuation of the first switch element and to activate a rotational movement of the tool in the right direction by the permanent or brief actuation of the second switch element. In this context, the two switch elements are preferably arranged in the pistol grip section, further preferably in an outer side region of the pistol grip section that is freely accessible by the remaining fingers of the hand of the operator during the rotation and/or pivoting the cardanically suspended tweezer element.

In another alternative embodiment of the present disclosure, the leg section comprises an upper leg section and a lower leg section, wherein the upper leg section and the lower leg section are pivotable together about a first pivot axis, in particular in order to manipulate the tool designed as a jaw part. In addition, the upper leg section is mounted pivotably relative to the lower leg section about a second pivot axis, wherein the second pivot axis is in particular oriented orthogonally to the first pivot axis. In other words, the control of the second handling mode can preferably be realized by pivoting the upper leg section relative to the lower leg section, in order thereby to control the endless or permanent rotation of the tool.

Through the preferred orthogonal orientation of the first pivot axis with respect to the second pivot axis, the first handling mode can advantageously be controlled and/or operated independently of the second handling mode. In other words, at the same time as introducing a pivoting movement for joint pivoting of the upper leg section and the lower leg section, a further pivoting movement for pivoting the upper leg section relative to the lower leg section can be introduced into the tweezer element, in order to directly control the endless rotation of the tool or to activate the second handling mode.

In a further development of the present disclosure, an end region of the leg section comprises a finger loop, which is preferably formed in a ring shape, in order to be able to introduce an opposing force for returning the leg sections into the tweezer element when the leg sections are pivoted.

The finger loop is thus arranged to receive the finger and the thumb at the end of the leg section, and it is dimensioned in diameter such that it is designed for receiving an index finger and/or a thumb.

Particularly preferably, the finger loops are arranged at the end of the upper leg section, since in this way a force for pivoting the upper leg section relative to the lower leg section can be introduced particularly easily into the tweezer element.

Finally, in the context of another preferred embodiment, it is provided that the tweezer element comprises energy storage means, wherein the leg sections are pivotable, counter to the force of the energy storage means, from the rest position about the first pivot axis and/or the second pivot axis, in order to realize an automated and/or automatic resetting of the leg sections to the rest position by the energy storage means after a manual pivoting of the leg sections. In this context, it is particularly preferred if the energy storage means are formed as a spring element, in particular a tension spring or compression spring. This advantageously simplifies the operation of the first handling mode and/or the second handling mode for controlling the tool, since only a unidirectional force, i.e. a force exerted in one direction, has to be introduced into the leg sections by the operator.

In addition, in the context of the present disclosure, protection is claimed for a medical system, in particular an end effector and/or a surgical robot, which has at least one input unit according to the disclosure and a medical instrument.

The medical instrument comprises a hollow shaft extending along a longitudinal axis, a control unit, and a tool for surgical use.

The shaft is designed for receiving steering wires for mechanically controlling the tool, wherein the tool is arranged at a distal end of the shaft and extends along an axis of extent.

Arranged at the proximal end of the shaft is the control unit, which is operatively connected to the tool via the steering wires, in order to pivot the tool in a first handling mode, in particular to pivot and rotate it to a limited extent, wherein the tool can also be rotated endlessly via the control unit in a second handling mode.

A preferred medical instrument is described in DE 10 2019 121 092 A1 of the applicant, with reference being made in full to the corresponding disclosure, and the disclosed features of the medical instrument, in the context of a further development, are incorporated in their entirety into the application.

Preferably, the medical instrument has a spatially adjustable plate for pivoting the steering wires along the longitudinal axis of the shaft, wherein the plate, together with the shaft and the steering wires, is rotatable about the longitudinal axis, and wherein the control unit is preferably designed for pivoting the plate.

The tool is preferably designed as a jaw part, in particular a jaw clamp, a plier, intestinal holding forceps, scissors, a needle holder, a probe hook or similar surgical tool.

Further advantages and details of the disclosure will become clear from the following description of preferred embodiments of the disclosure and from the drawings, which are merely schematic.

Further embodiments, and some of the advantages associated with these and with further embodiments, are made clear and more understandable by the following detailed description which makes reference to the attached figures. Objects or parts thereof which are substantially the same or similar may be provided with the same reference signs. The figures are merely a schematic illustration of an embodiment of the disclosure. An exemplary embodiment of the disclosure is depicted in the drawings. The drawings, the description and the claims contain numerous features in combination. A person skilled in the art will advantageously also consider the features on an individual basis and combine them to form further advantageous combinations.

BRIEF DESCRIPTION OF DRAWINGS

FIG. 1 shows a perspective view of a medical instrument with a purely symbolically represented input unit according to the disclosure.

DETAILED DESCRIPTION OF PREFERRED EMBODIMENTS

Figures 2A, 2B, 2C:
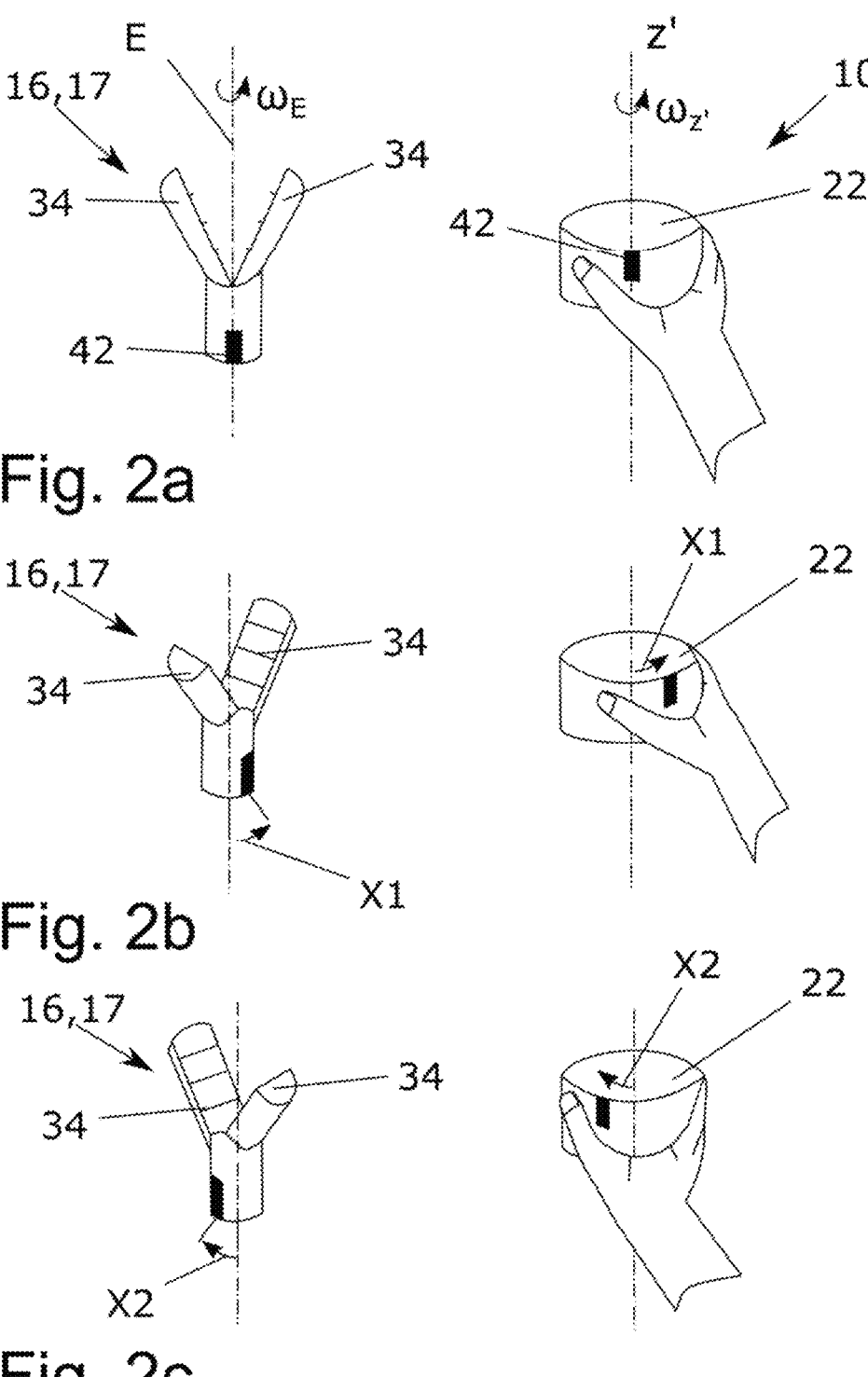
FIG. 2a to FIG. 2c show a perspective view of a tool of the medical instrument according to FIG. 1, and schematically depicted first input means of the input unit according to the disclosure.

The same elements, or elements having the same function, are provided with the same reference numbers in the figures.

Figure 1:
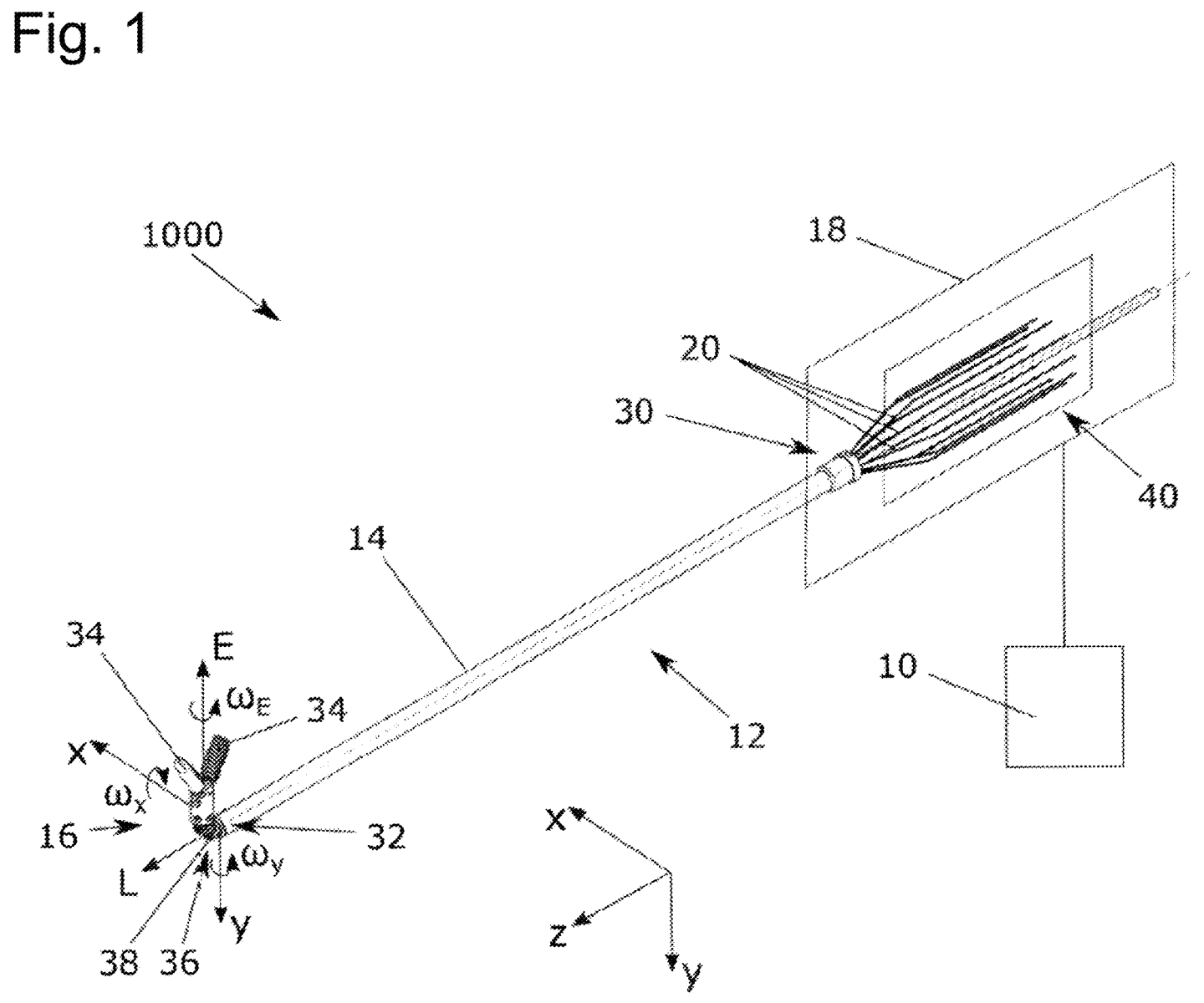

FIG. 1 shows a medical system 1000 with a medical instrument 12, which can be operated by means of an input unit 10 of the disclosure designed as a black box. The medical instrument 12 has a hollow shaft 14 which, at a proximal end 30, comprises a control unit 18, shown as a black box, and which, at a distal end 32, comprises a tool 16, wherein the tool 16 is operatively connected to the control unit 18 via steering wires 20.

The control unit 18 enables an endless rotational drive of the tool 16, pivoted by 90° as shown in the figure. For this purpose, for example, a control unit 18 can be used of the kind known from the already mentioned DE 10 2019 121 092 A1 of the applicant.

The tool 16 is a tool 16 provided with jaw elements 34, in particular a jaw part 17, wherein the jaw elements 34 are also adjustable via the control unit 18 like pliers between an opened state and a closed state, in order to realize the gripping functionality of the jaw part 17.

The tool 16 is pivotable relative to the longitudinal axis L of the shaft 14 by way of a joint mechanism 36, wherein the joint mechanism 36 consists of pivot members 38 which are arranged at the distal end 32 of the shaft 14 and are connected via steering wires 20 running in the longitudinal direction L of the shaft 14 to a drive 40 (not shown in the figure) arranged at the proximal end 30 of the shaft 14, in such a way that a movement of the proximal-side drive 40 causes a corresponding relative movement of the distal-side pivot members 38 and hence a pivoting of the tool tip 16.

A corresponding drive 40 is known, for example, from the already mentioned DE 10 2019 121 092 A1 of the applicant. There, the steering wires 20 are connected proximally to a plate (not shown in the figures), which can be pivoted and rotated spatially by means of the drives 40. The pivoting of the plate has the effect that the steering wires 20 partially tension along the longitudinal axis L of the shaft 14 and that the tool 16, extending in a z-direction of a Cartesian coordinate system, can pivot proportionately about the spatial axes x, y of the Cartesian coordinate system by means of the joint mechanism 36. The pivoting movements $\omega_x$, $\omega_y$ about the spatial axes x, y thus allow a spatial orientation of the tool 16.

Through the rotation of the shaft 14 together with the steering wires 20 about the longitudinal axis L, the tool 16 can also be rotated permanently or endlessly relative to the control unit 18. Through the use of the pivotably and rotatably mounted plate, the tool 16 can be adjusted simultaneously for a permanent rotation about the longitudinal axis L also by the steering wires 20 along the longitudinal axis L. Thus, the spatial orientation of the tool 16 can be compensated during the permanent rotation of the shaft 14, wherein the tool 16 rotates about its axis of extent E with a rotational movement $\omega_E$. If the tool 16 is in a non-pivoted state, the axis of extent E of the tool 16 corresponds to the longitudinal axis L of the shaft 14, i.e. extends in the z-direction of the Cartesian coordinate system.

Since the steering wires 20 together with the shaft 14 can rotate about the longitudinal axis L, an endless rotation about the longitudinal axis L or the axis of extent E by means of the drive 40 can be realized without the steering wires 20 twisting into each other to form a cord and limiting or preventing control of the pivoting movement $\omega_x$, $\omega_y$.

To illustrate the functioning of the first input means 22 of the input unit 10 according to the disclosure, FIG. 2a to FIG. 2c show in schematic form the operating principle involved in converting an ergonomically limited user input of an operator into a manipulation of the tool 16 formed as jaw part 17.

FIG. 2a shows the input unit 10 and the jaw part 17 in a rest position or a basic position, each with markings 42 to illustrate the orientation.

In the present case, the first input means 22 are designed as a graspable cylinder, which is in operative contact with the control unit 18 (not shown) by means of a gimbal suspension (not shown).

For simplification, it is assumed that the ergonomically limited user input is limited only to a rotation of the jaw part 17 about the axis of extent E in the first handling mode, which is why the degree of freedom of movement of the arm or hand limits the range of rotation.

In the first handling mode, the rotational movement $\omega_z$, of the first input means 22 and the rotational movement DE of the tool 16 are rotationally true to each other, i.e. they have the same angular velocities.

In FIG. 2b, the first input means 22 were rotated counterclockwise by a first angular range X1, wherein this rotational movement was transferred at the true angle to the jaw part 17. Moreover, the first input means 22 were then rotated clockwise in relation to FIG. 2c from the position shown in FIG. 2b by a second angular range X2, and here too the jaw part 17 follows the rotational movement of the first input means 22 at the true angle.

The operator's hand remains in contact with the first input means 22 during the ergonomically limited user input. Thus, in the first handling mode, there should be no gripping or brief interruption between the input unit and the tool, since the aim is to realize a continuous and preferably uninterrupted mapping of the rotational movement $\omega_z$, introduced into the first input means 22, into the rotational movement DE of the jaw part 17. An operator therefore has continuous and uninterrupted control over the adjustment movement of the tool 16, in particular in order to be able to perform precise and complex minimally invasive procedures and/or medical operations in a sensitive environment.

Due to the physiology of the human hand, the rotation range is limited to a maximum rotation angle of about +90° around the rest position and thus to a total of about 180° around the rest position or basic position.

Figures 3A, 3B, 3C:
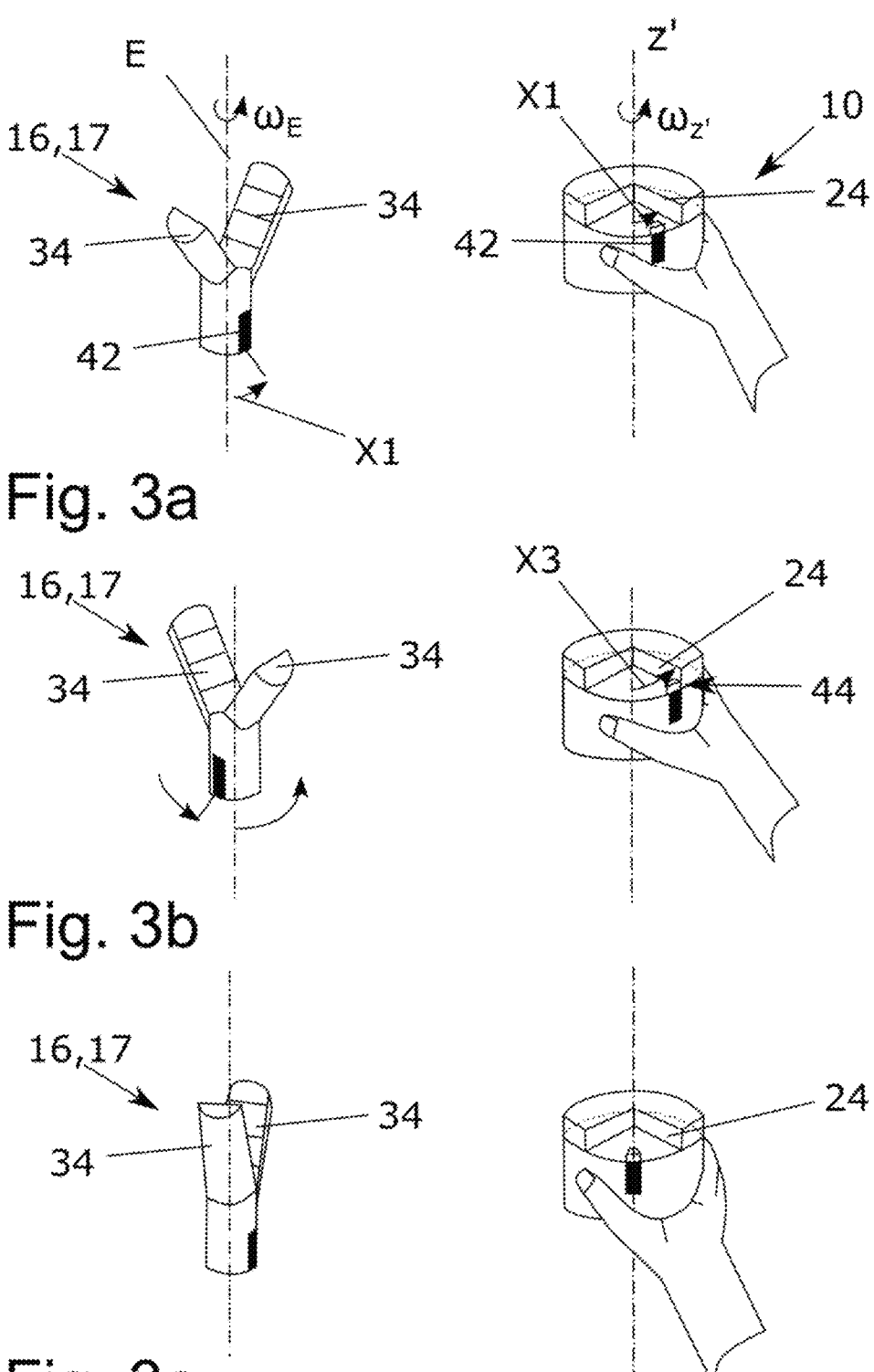
FIG. 3a to FIG. 3c show a perspective view of the known tool from FIG. 2, and schematically depicted second input means of the input unit according to the disclosure.

In FIG. 3a to FIG. 3c, in addition to the control of the tool 16 in the first handling mode, the control of the tool 16 is also effected via the second input means 24 in the second handling mode.

In the present case, the second input means 24 are formed by the identical graspable cylinder in order to realize the control of the tool 16 both in the first handling mode and in the second handling mode.

In FIG. 3a, as already in FIG. 2b, the first input means 22 and thus also the second input means 24 are shown rotated counterclockwise from the basic position of FIG. 2a about the angular range X1, wherein the angular range X1 was mapped with the correct rotation onto the jaw part 17 and causes a corresponding rotation. This means that the tool is controlled in the first handling mode.

In FIG. 3b, by means of a further user movement, the cylinder was rotated about the third angular range X3, greater than the first angular range X1, as a result of which the second input means 24 were guided into an end stop 44, in which an endless rotational movement of the jaw part 17 is activated. The jaw part 17 thus rotates endlessly about its axis of extents E as a result of further user input 21.

When the second input means 24 return to the basic position according to FIG. 3c, the endless rotation of the tool 16 is interrupted again. In this case, the tool 16 does not follow the movement of the second input means 24 back to the basic position, such that the position of the markings 42 of the tool 16 and of the input unit 10 can be adjusted relative to each other. In the second handling mode, it is thus advantageously made possible by the second input means 24 that, in contrast to the operating principle of the first input means described in relation to FIG. 2b and FIG. 2c in the first handling mode, the speed of the rotational movement $\omega_E$ is at least in part is not converted in a rotationally true manner according to the further user input. However, the further user input is still coupled without interruption to the rotational movement $\omega_E$ of the tool 16, in order to ensure complete control of the tool movement at all times. The ergonomically operable rotation range is advantageously extended from the approximately ±90° about the rest position or basic position by the second input means 24, without the operator losing control over the jaw part 17.

Figure 4:
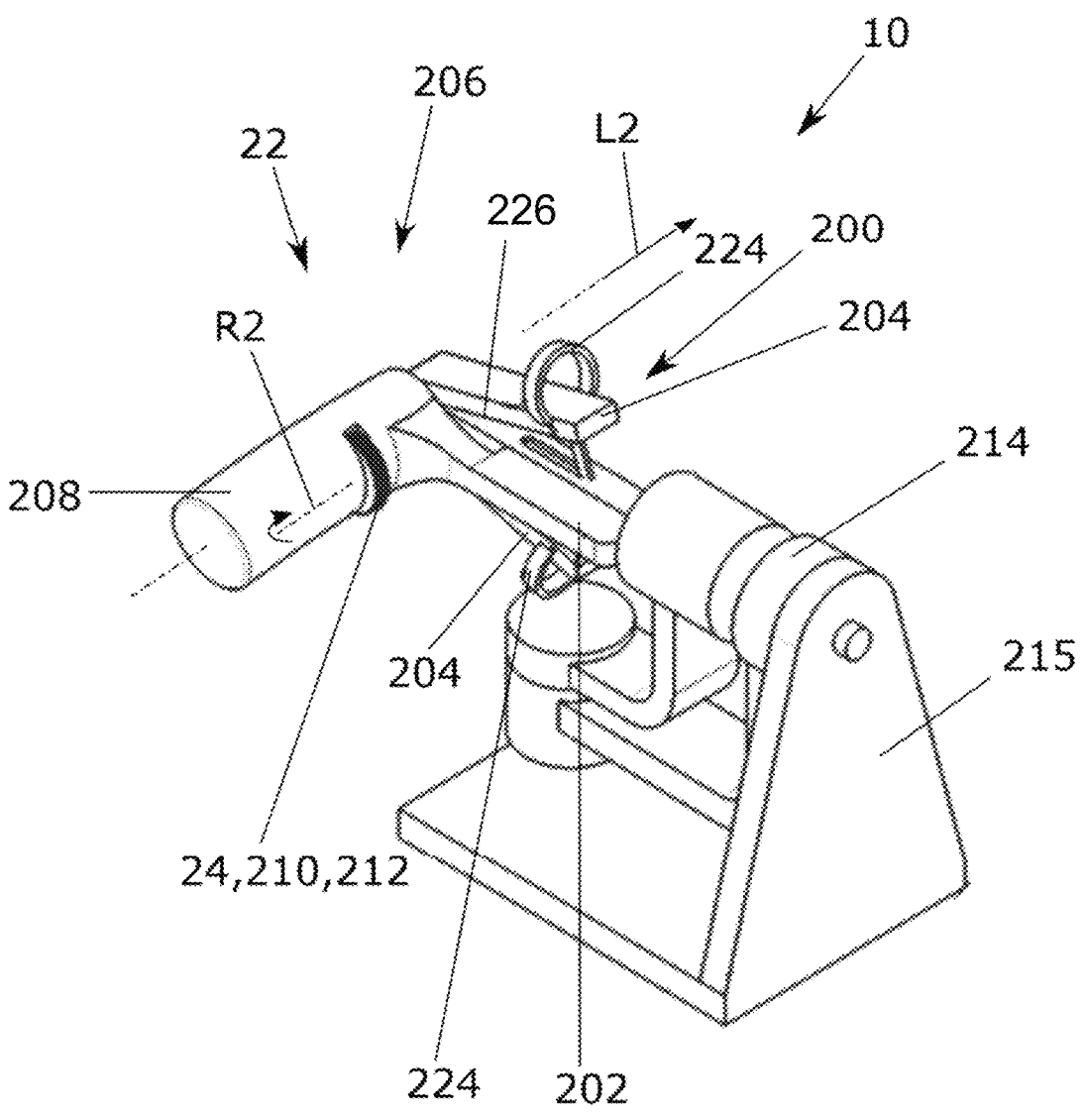
FIG. 4 shows a first embodiment of the input unit according to the disclosure.

FIG. 4 shows a first embodiment of the input unit 10 according to the disclosure for operating the endlessly rotatable medical instrument 12 known from FIG. 1.

The illustrated input unit 10 according to the disclosure comprises first input means 22, which are designed for continuous, pivotably and/or rotationally accurate detection and imaging of an ergonomically limited user input of the operator into an adjustment movement of the tool 16 in a first handling mode, in order to pivot the tool 16 to a limited extent relative to the longitudinal axis L of the shaft 14 and/or to rotate the axis of extent E of the tool 16.

For detecting the ergonomically limited user input of the operator, the first input means 22 comprise first operating means, which in the present case are formed by a cardanically suspended tweezer element 200.

The gimbal suspension 214 comprises a stationary, L-shaped stand element 215 which, by way of at least two rotary bearings, fixes and orients the tweezer element 200 by a carrier element 202 comprised by the tweezer element 200.

The tweezer element 200 comprises two leg sections 204, which are pivotable relative to each other about a common pivot axis or about two mutually parallel pivot axes, in such a way that the two leg sections 204 move toward each other during the pivoting.

Advantageously, the two leg sections 204 extend in such a way that they can be gripped between thumb and index finger in a working position of the operator, in order to introduce a force into both leg sections 204 and thus pivot them from the rest position 206 shown in the figure. Through the pivoting of the two leg sections 204, the tool 16 is advantageously manipulated, it being particularly preferable in this context if the tool 16 is designed as a jaw part 17 or equivalent action unit, which can thus be manipulated between an open and a closed position, in particular to control a cutting and/or gripping functionality.

Further, the tweezer element 200 according to the disclosure comprises a pistol grip section 208, the longitudinal extent of which is oriented substantially transverse to the longitudinal extent of the leg sections 204. The pistol grip section 208 of the tweezer element 200 serves as a palm rest for the operator in the working position, which is why a precise and ergonomic operation of the tweezer element 200 is made possible.

Thus, in the context of detecting the ergonomically limited user input, it is not only provided that the two leg sections 204 are pivoted, but also that the entire tweezer element 200 is adjusted from the illustrated rest position 206 on account of the gimbal suspension, wherein the pivoting and/or rotational movements of the tweezer element 200, that is to say all the adjustment movements from the rest position 206 shown in the figure in the first handling mode, are detected and are applied to the tool 16 in a pivotably and rotationally true manner.

Moreover, the pistol grip section 208 comprises second input means 24 according to the disclosure, which are arranged as second operating means 210 on a side surface of the pistol grip section 208. In the present case, the second operating means 210 are formed by a plate-shaped and round rotary element 212, which in part radially protrudes beyond the cylindrical pistol grip section 208 in such a way that it is advantageously possible that, in the working position of the operator, the rotary element 212 can be operated by means of the remaining fingers of the hand that is used for pivoting the leg sections 204. When the hand of the operator is supported by the pistol grip section 208, it is thus advantageously possible to adjust the tweezer element 200, wherein in addition the second input means 24 can also be operated. Advantageously, this leads to an ergonomic design of the input unit 10, in order to enable precise control of the tool 16 in the first handling mode and in the second handling mode, even during longer operations.

In the present case, the rotary element 212 shown in the figure is infinitely rotatable, wherein the rotational movement of the rotary element 212 is applied to the tool 16 in a rotationally true or scaled manner. In addition, the tweezer element 200 preferably comprises switching means in order to switch the transmission function in the second handling mode between an absolute and/or unscaled and a scaled transmission or between a first scaling and a second scaling.

Furthermore, an alternative embodiment of the rotary element 212 is preferably also provided, wherein the rotary element 212 is rotatable from a rest position along a first direction of rotation to a first end position, wherein an activation of an endless rotation of the tool 16 into a first direction is activated in the first end stop. To end the rotational movement, the rotary element 212 must then be returned to the rest position. To activate an opposite rotational movement of the tool 16, the rotary element 212 has to be rotated from the rest position along a second, opposite direction of rotation to a second end position.

Moreover, in an end portion of the leg sections 220, annular finger loops 224 are arranged for receiving thumb and index finger, these permitting the return of the leg sections 220 to the rest position 206 by application of a counterforce.

In addition, the tweezer element 200 comprises energy storage means 226 (not shown in detail), which allow the automated return of the leg sections 204 to the rest position.

Figure 5:
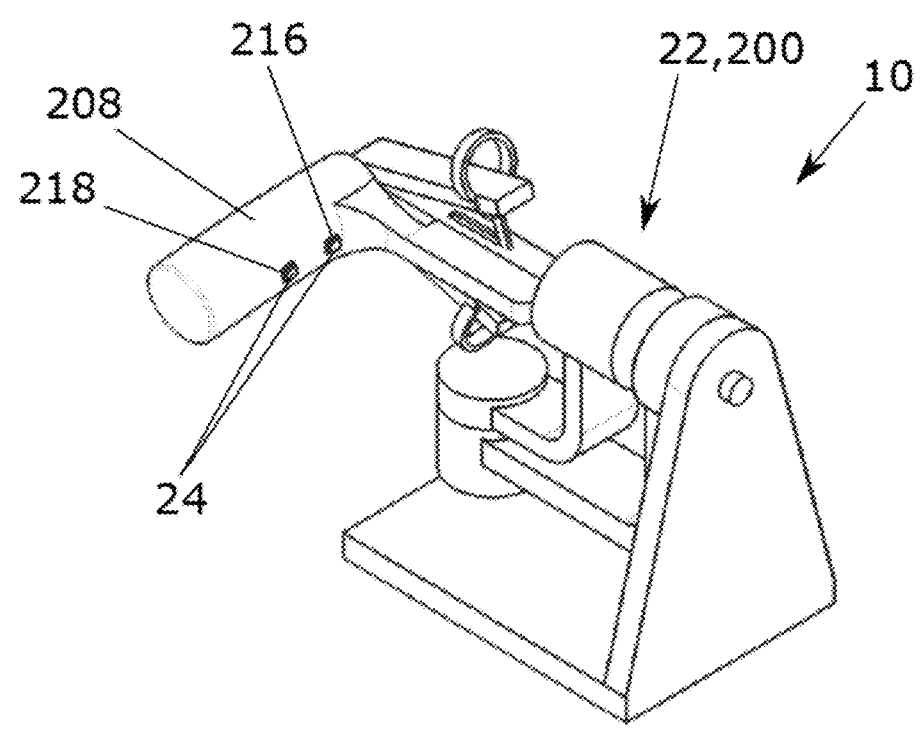
FIG. 5 shows a second embodiment of the input unit according to the disclosure.

FIG. 5 shows a further embodiment of the input unit 10 according to the present disclosure. The input unit 10 shown in the figure comprises first input means 22 according to the disclosure and second input means 24 according to the disclosure.

The first input means 22 for the continuous, pivotably and/or rotationally true conversion of an ergonomically limited user input into an adjustment movement of the tool 16 in the first handling mode are also formed by a cardanically suspended tweezer element 200, for which reason reference is made to the previous embodiment in order to avoid repetition.

In contrast to the previous exemplary embodiment, the second input means 24 according to the disclosure are now formed by a first switch element 216 and a second switch element 218, which are arranged in a side surface of the pistol grip section 208. The two switch elements 216, 218 can be actuated by application of force, in order to activate the activation of an endless rotation of the tool 16. The direction of the rotational movement of the tool 16 depends on which switch element 216, 218 is pressed. Moreover, continuous rotation is made possible by subsequent pressing of the other switch element.

Thus, the direction of rotation can first be selected by actuating one of the two switch elements 216, 218, after which, by actuating the switch element 216, 218 not yet actuated, a continuous rotation of the tool 16 can be activated. The tool 16 can thus be operated particularly precisely and ergonomically in the second handling mode.

Figure 6:
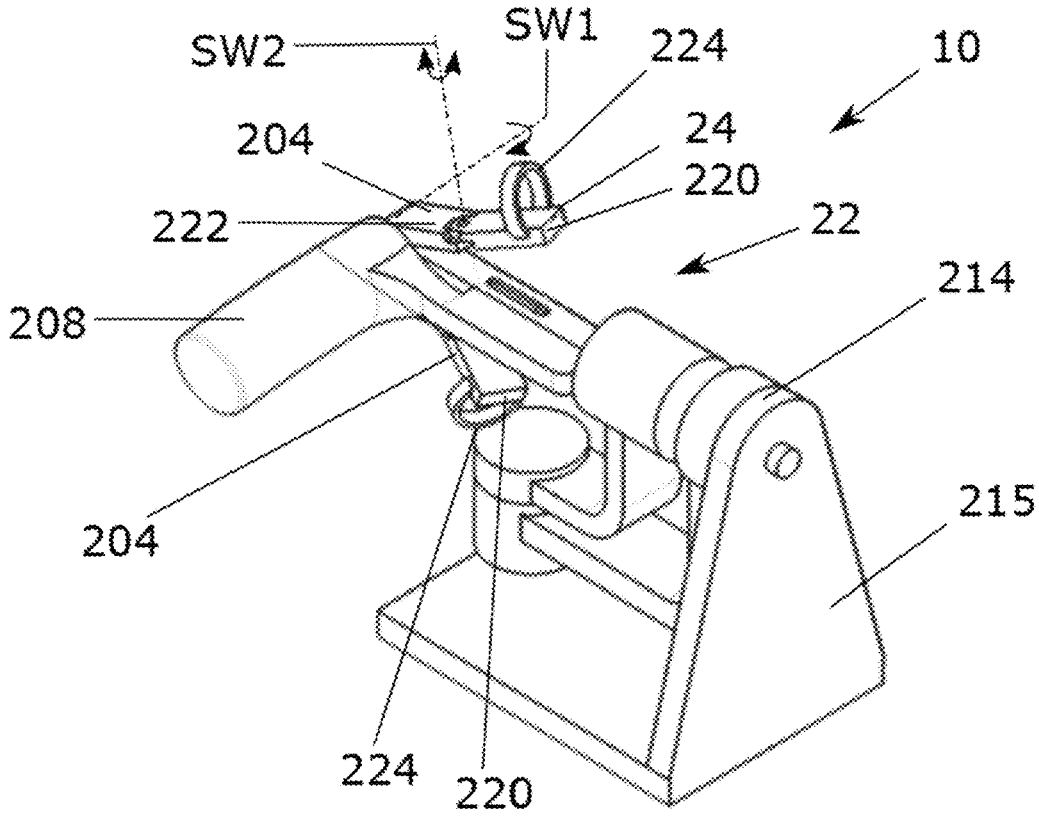
FIG. 6 shows a third embodiment of the input unit according to the disclosure.

Finally, FIG. 6 shows another preferred embodiment of the input unit 10 according to the disclosure. The input unit 10 shown again comprises, for the configuration of the first input means 22, a cardanically suspended tweezer element 200 which, together with a pistol grip section 208, is adjustable relative to the stand element 215 of the gimbal suspension 214, so that all the ergonomically limited user inputs, such as pivoting and/or rotational movements, can be applied to the tool 16 in a pivotably and/or rotationally true manner in the first handling mode.

As is also already known in relation to the other exemplary embodiments, in addition to the rotation and pivoting of the entire tweezer element 200, the two leg sections 204 can also be pivoted relative to each other in order to manipulate the tool 16, in particular to control the closing position of the jaw part 17.

In the embodiment now shown, the second input means 24 are formed by a further pivoting mechanism of the leg sections 204. Thus, the leg section 204 comprises an upper leg section 220 and a lower leg section 222, which can be pivoted relative to each other to a limited extent about a second pivot axis SW2, in order thereby to take up the further user input for the control of the tool 16 in the second handling mode.

Moreover, the upper leg section 220 and the lower leg section 222 can be pivoted together about a first pivot axis SW1 in order to realize the pivotably true manipulation of the tool 16 in the first handling mode. Irrespective of this pivoting movement, it is also possible to pivot the upper leg section 220 relative to the lower leg section 222 about the second pivot axis SW2: it will be seen from the depiction in the figure that the orientation of the first pivot axis SW1 is at a right angle to the second pivot axis SW2.

Moreover, in this embodiment too, a finger loop 224 is provided at the end of the leg section 204, in order in particular to apply a force for pivoting the upper leg section 220 relative to the lower leg section 222.

The drawings, the description and the claims contain numerous features in combination. A person skilled in the art will advantageously also consider the features on an individual basis and combine them to form further advantageous combinations. The disclosure relates to an input unit 10 for operating a medical instrument 12, comprising: a hollow shaft 14 extending along a longitudinal axis L for receiving steering wires 20: a tool 16 which is arranged at the distal end of the shaft 14 and is formed along an axis of extent E; and a control unit 18, which is arranged at the proximal end of the shaft 14, for manipulating the tool 16 by means of the steering wires 20, the input unit comprising first input means 22 for continuously converting, in a pivotably and/or rotationally true manner and preferably without interruption and/or absolutely, an ergonomically limited user input, in particular a natural user movement of movable first operating means, into an adjustment movement of the tool 16 in a first handling mode, in order to pivot the tool 16 to a limited extent relative to the longitudinal axis L and/or rotate it to a limited extent about the axis of extent E by means of the control unit 18.

The invention claimed is:

1. An input unit for operating a medical instrument including: a hollow shaft extending along a longitudinal axis for receiving steering wires; a tool which is arranged at a distal end of the shaft and is formed along an axis of extent; and a control unit, which is arranged at a proximal end of the shaft, for manipulating the tool by means of the steering wires, the input unit comprising:

a first input means for continuously converting, in a pivotably and/or rotatable 360 degrees about a rotational axis, an ergonomically limited user input rotatable +−90 degrees comprising a natural user movement of a movable first operating means, into an adjustment movement of the tool in a first handling mode, in order to pivot the tool to a limited extent relative to the longitudinal axis and/or rotate the tool to a limited extent about the axis of extent by means of the control unit; and a second input means for at least partially, non-absolutely converting at least one further user input into an endless rotational movement of the tool about the axis of extent of the tool in a second handling mode, wherein the first input means are formed by a tweezer element suspended cardanically via a carrier element and including two leg sections which are oriented and formed in such a way that they can be gripped between a thumb and an index finger of an operator in a working position in order to move the two leg sections toward each other from a rest position by means of an application of a force, in order to manipulate a jaw part of the tool, wherein the tweezer element includes a pistol grip section formed as a unitary part of the tweezer element and designed for placing a palm of the operator's hand in the working position, and wherein the second input means is designed as a second operating means either on the pistol grip section or on one or both of the two leg sections, wherein the second operating means is formed by a rotary element or a rocker element, which is received by and/or arranged on a lateral outer surface of the pistol grip section, and wherein the rotary element is rotatable about an axis of rotation which runs substantially parallel to an axis of longitudinal extent of the pistol grip section.

2. The input unit as set forth in claim 1, wherein one of the rotary element or the rocker element is received by and/or arranged on a lateral outer surface of the pistol grip section and protrudes in some regions such that the second operating means can be rotated or actuated, in the working position of the operator, by remaining fingers of the hand used to pivot the two leg sections, in order to serve the further user input.

3. The input unit as set forth in claim 2, wherein the rotary element is rotatable from a rest position along a positive angular range into a positive end stop and along a negative angular range into a negative end stop, in order to rotate the tool in the positive end stop in a first direction and in the negative end stop in a second direction counter to the first direction by the further user input.

4. The input unit as set forth in claim 1, wherein each of the two leg sections includes an upper leg section and a lower leg section, and wherein the upper leg sections and the corresponding lower leg sections can be pivoted together about a first pivot axis to manipulate the jaw part, and wherein the upper leg sections can be pivoted relative to the corresponding lower leg sections about a second pivot axis, in order to control the further user input to rotate the jaw part, wherein the second pivot axis is oriented orthogonally to the first pivot axis.

5. The input unit as set forth in claim 4, wherein at least one of the upper leg sections, includes an annular finger loop, which is arranged at the end of the upper leg section.

6. The input unit as set forth in claim 1, wherein the tweezer element includes an energy storage means, wherein the two leg sections are pivotable from the rest position counter to the force of the energy storage means.

7. The input unit as set forth in claim 2, wherein the rotary element or the rocker element is one of a rotary wheel, a gauge wheel or a rocker switch.

8. An input unit for operating a medical instrument including: a hollow shaft extending along a longitudinal axis for receiving steering wires; a tool which is arranged at a distal end of the shaft and is formed along an axis of extent; and a control unit, which is arranged at a proximal end of the shaft, for manipulating the tool by means of the steering wires, the input unit comprising:

a first input means for continuously converting, in a pivotably and/or rotatable 360 degrees about a rotational axis, an ergonomically limited user input rotatable +−90 degrees comprising a natural user movement of a movable first operating means, into an adjustment movement of the tool in a first handling mode, in order to pivot the tool to a limited extent relative to the longitudinal axis and/or rotate the tool to a limited extent about the axis of extent by means of the control unit; and a second input means for at least partially, non-absolutely converting at least one further user input into an endless rotational movement of the tool about the axis of extent of the tool in a second handling mode, wherein the first input means are formed by a tweezer element suspended cardanically via a carrier element and including two leg sections which are oriented and formed in such a way that they can be gripped between a thumb and an index finger of an operator in a working position in order to move the two leg sections toward each other from a rest position by means of an application of a force, in order to manipulate a jaw part of the tool, wherein the tweezer element includes a pistol grip section formed as a unitary part of the tweezer element and designed for placing a palm of the operator's hand in the working position, and wherein the second input means is designed as a second operating means either on the pistol grip section or on one or both of the two leg sections, wherein the second operating means is formed by at least one switch element for switching between the first handling mode and the second handling mode, wherein in the second handling mode the tweezer element is rotatable from the rest position into a left end stop and into a right end stop, wherein a permanent left rotation movement of the tool is able to be activated in the left end stop and a permanent right rotation movement of the tool is able to be activated in the right end stop.

9. An input unit for operating a medical instrument including: a hollow shaft extending along a longitudinal axis for receiving steering wires; a tool which is arranged at a distal end of the shaft and is formed along an axis of extent; and a control unit, which is arranged at a proximal end of the shaft, for manipulating the tool by means of the steering wires, the input unit comprising:

a first input means for continuously converting, in a pivotably and/or rotatable 360 degrees about a rotational axis, an ergonomically limited user input rotatable +−90 degrees comprising a natural user movement of a movable first operating means, into an adjustment movement of the tool in a first handling mode, in order to pivot the tool to a limited extent relative to the longitudinal axis and/or rotate the tool to a limited extent about the axis of extent by means of the control unit; and a second input means for at least partially, non-absolutely converting at least one further user input into an endless rotational movement of the tool about the axis of extent of the tool in a second handling mode, wherein the first input means are formed by a tweezer element suspended cardanically via a carrier element and including two leg sections which are oriented and formed in such a way that they can be gripped between a thumb and an index finger of an operator in a working position in order to move the two leg sections toward each other from a rest position by means of an application of a force, in order to manipulate a jaw part of the tool, wherein the tweezer element includes a pistol grip section formed as a unitary part of the tweezer element and designed for placing a palm of the operator's hand in the working position, and wherein the second input means is designed as a second operating means either on the pistol grip section or on one or both of the two leg sections, wherein the second operating means includes a first switch element and a second switch element, wherein the first switch element is designed such that, by permanent or brief actuation of the first switch element, a first switching state can be activated in order to activate a permanent left rotational movement of the tool, and wherein the second switch element is designed such that, by permanent or brief actuation of the second switch element, a second switching state can be activated in order to activate a permanent right rotation movement of the tool.

10. The input unit as set forth in claim 9, wherein at least one of the first switch element and the second switch element is/are arranged on a side surface of the pistol grip section, such that, in the working position of the operator, the first switch element and the second switch element can be actuated by remaining fingers of the corresponding hand provided for pivoting the two leg sections.

* * * * *